(12) United States Patent
Raines et al.

(10) Patent No.: US 8,337,533 B2
(45) Date of Patent: Dec. 25, 2012

(54) LOCKING PLATE BENDERS

(75) Inventors: Aaron Truett Raines, Dallas, TX (US); Brandon G. Beckendorf, Arlington, TX (US); Lisa R. Thornhill, Dallas, TX (US)

(73) Assignee: Osteomed LLC, Addison, TX (US)

( * ) Notice: Subject to any disclaimer, the term of this patent is extended or adjusted under 35 U.S.C. 154(b) by 1193 days.

(21) Appl. No.: 12/143,378

(22) Filed: Jun. 20, 2008

(65) Prior Publication Data

US 2009/0318979 A1    Dec. 24, 2009

(51) Int. Cl.
*A61B 17/80* (2006.01)
(52) U.S. Cl. .......................... 606/284; 606/291
(58) Field of Classification Search .................. 606/291, 606/281–285, 280, 279, 246–257
See application file for complete search history.

(56) References Cited

U.S. PATENT DOCUMENTS

| | | | | |
|---|---|---|---|---|
| 5,468,242 | A * | 11/1995 | Reisberg | 606/285 |
| 5,752,958 | A * | 5/1998 | Wellisz | 606/285 |
| 5,779,706 | A * | 7/1998 | Tschakaloff | 606/281 |
| 5,851,207 | A * | 12/1998 | Cesarone | 606/86 B |
| 5,954,722 | A * | 9/1999 | Bono | 606/281 |
| 6,102,951 | A * | 8/2000 | Sutter et al. | 623/18.11 |
| 6,712,818 | B1 * | 3/2004 | Michelson | 606/281 |
| 7,273,481 | B2 * | 9/2007 | Lombardo et al. | 606/86 A |
| 7,357,804 | B2 * | 4/2008 | Binder et al. | 606/96 |
| 7,476,228 | B2 * | 1/2009 | Abdou | 606/104 |
| 7,625,381 | B2 * | 12/2009 | Michelson | 606/105 |
| 7,717,942 | B2 * | 5/2010 | Schumacher | 606/266 |
| 7,740,634 | B2 * | 6/2010 | Orbay et al. | 606/101 |
| 7,763,029 | B2 * | 7/2010 | Rathbun et al. | 606/96 |
| 7,771,433 | B2 * | 8/2010 | Orbay et al. | 606/101 |
| 7,905,910 | B2 * | 3/2011 | Gerlach et al. | 606/291 |
| 7,955,362 | B2 * | 6/2011 | Erickson et al. | 606/289 |
| 7,985,229 | B2 * | 7/2011 | Stihl | 606/96 |
| 8,025,677 | B2 * | 9/2011 | Freid et al. | 606/246 |
| 2002/0042654 | A1 * | 4/2002 | Masini | 623/22.32 |
| 2003/0083667 | A1 * | 5/2003 | Ralph et al. | 606/96 |
| 2004/0102777 | A1 * | 5/2004 | Huebner | 606/69 |
| 2005/0165401 | A1 * | 7/2005 | Pack | 606/69 |
| 2005/0234467 | A1 * | 10/2005 | Rains | 606/96 |
| 2009/0036933 | A1 * | 2/2009 | Dube et al. | 606/282 |
| 2009/0076556 | A1 * | 3/2009 | McGarity et al. | 606/281 |
| 2009/0248084 | A1 * | 10/2009 | Hintermann | 606/286 |
| 2009/0312760 | A1 * | 12/2009 | Forstein et al. | 606/71 |
| 2010/0057086 | A1 * | 3/2010 | Price et al. | 606/70 |
| 2010/0100134 | A1 * | 4/2010 | Mocanu | 606/281 |
| 2010/0106196 | A1 * | 4/2010 | Erickson et al. | 606/281 |

(Continued)

OTHER PUBLICATIONS

Synthes Technique Guide, The Locking Calcaneal Plate. Part of the Synthes small fragment Locking Compression Plate (LCP) System, 2007.

*Primary Examiner* — Alvin J. Stewart
(74) *Attorney, Agent, or Firm* — Baker Botts L.L.P.

(57) ABSTRACT

A system for contouring a locking plate includes a locking plate and at least one bender. The locking plate includes a plurality of threaded screw holes connected to one another by one or more ribs. The at least one bender includes a threaded tip configured to threadably engage one or more of the plurality of threaded screw holes and a shoulder operable to transmit mechanical force to the locking plate once the threaded tip is threadably engaged with one of the plurality of threaded screw holes.

6 Claims, 5 Drawing Sheets

U.S. PATENT DOCUMENTS

| | | |
|---|---|---|
| 2010/0179600 A1* | 7/2010 | Steger et al. .................. 606/281 |
| 2010/0185246 A1* | 7/2010 | Castaneda et al. ............ 606/305 |
| 2010/0262193 A1* | 10/2010 | Frigg et al. .................... 606/281 |
| 2010/0324603 A1* | 12/2010 | Mohr et al. .................... 606/281 |
| 2011/0060370 A1* | 3/2011 | Worcel .......................... 606/281 |
| 2011/0166607 A1* | 7/2011 | Castaneda et al. ............ 606/291 |
| 2011/0184414 A1* | 7/2011 | Andermahr et al. ........... 606/70 |

* cited by examiner

LOCKING PLATE BENDERS

TECHNICAL FIELD

The present disclosure relates generally to repairing bone fractures, and more particularly, to a locking plate and locking plate benders.

BACKGROUND

When repairing a broken or fractured bone, a physician may often be faced with the task of contouring a locking plate to match bone anatomy (e.g., the curvature of a bone). Consequently, the physician may have to engage in a trial and error process of bending the locking plate and checking the contour of the locking plate against the contour of the fractured bone in order to achieve an acceptable fit.

SUMMARY

In particular embodiments, the present disclosure provides for a system and method for contouring a locking plate that includes a locking plate and at least one bender. The locking plate includes a plurality of threaded screw holes connected to one another by one or more ribs. The at least one bender includes a threaded tip configured to threadably engage one or more of the plurality of threaded screw holes and a shoulder operable to transmit mechanical force to the locking plate once the threaded tip is threadably engaged with one of the plurality of threaded screw holes.

In particular embodiments, once the threaded tip is threadably engaged with one of the plurality of threaded screw holes, the shoulder is operable to transmit a majority of the mechanical force from the bender to the locking plate and the threaded tip is operable to transmit a minority of the mechanical force to the locking plate.

In particular embodiments, the thickness of each of the one or more ribs may be less than the thickness of a rim surrounding each of the plurality of threaded screw holes to facilitate bending of the ribs when the mechanical force is applied to the locking plate.

In particular embodiments, the shoulder may include a first flat surface surrounding the threaded tip that is operable to transmit mechanical force to the locking plate once the threaded tip is threadably engaged with one of the plurality of threaded screw holes by abutting an opposing flat surface of a rim surrounding the threaded screw hole.

In particular embodiments, the at least one bender may include a shaft having a threaded extension and a shoulder piece engaged with a first portion of the threaded extension such that a second portion of the threaded extension extends through the shoulder piece to form the threaded tip of the bender.

In particular embodiments, the length of the threaded tip may be less than or equal to a thickness of a rim surrounding each of the plurality of threaded screw holes.

In particular embodiments, the shoulder may generally prevent the threaded tip from extending through one of the plurality of threaded screw holes once the threaded tip is threadably engaged with the screw hole. Furthermore, the bottom portion of the threaded tip may be flattened such that the bottom portion rests approximately flush with the bottom surface of the locking plate once the threaded tip is threadably engaged with the screw hole.

In particular embodiments, the at least one bender may be operable to press a bottom surface of the locking plate directly against a top surface of a bone once the threaded tip is threadably engaged with one of the plurality of threaded screw holes.

Technical advantages of particular embodiments of the present disclosure may include providing a system and method for contouring a locking plate whereby one or more benders may apply mechanical force to the locking plate using a shoulder to contour the locking plate while preserving the integrity of the locking threads on the inner surface of each of the screw holes in the locking plate. This technical advantage may lessen or eliminate the risk that a deformed threaded screw hole will prevent the locking plate from properly engaging one or more corresponding locking screws that may later be inserted into a fractured bone through the locking plate, yet another technical advantage of the present disclosure. As an additional technical advantage of the present disclosure, the one or more benders may be cannulated to allow a surgeon to align the bender with the locking plate in cramped working space (e.g., in the incision area) using a K-wire or positioning pin. Another technical advantage of the present disclosure may allow a surgeon to press the bottom surface of the locking plate directly against a bone without being hindered by the tip of the bender. Particular embodiments of the present disclosure may take advantage of on-bone benders and pliers to virtually eliminate the chance of the threaded portion (e.g., the threaded screw holes) of the locking plate from deforming when the locking plate is contoured.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and its advantages, reference is now made to the following descriptions, taken in conjunction with the accompanying drawings, in which.

DETAILED DESCRIPTION OF EXAMPLE EMBODIMENTS

Figure 1:
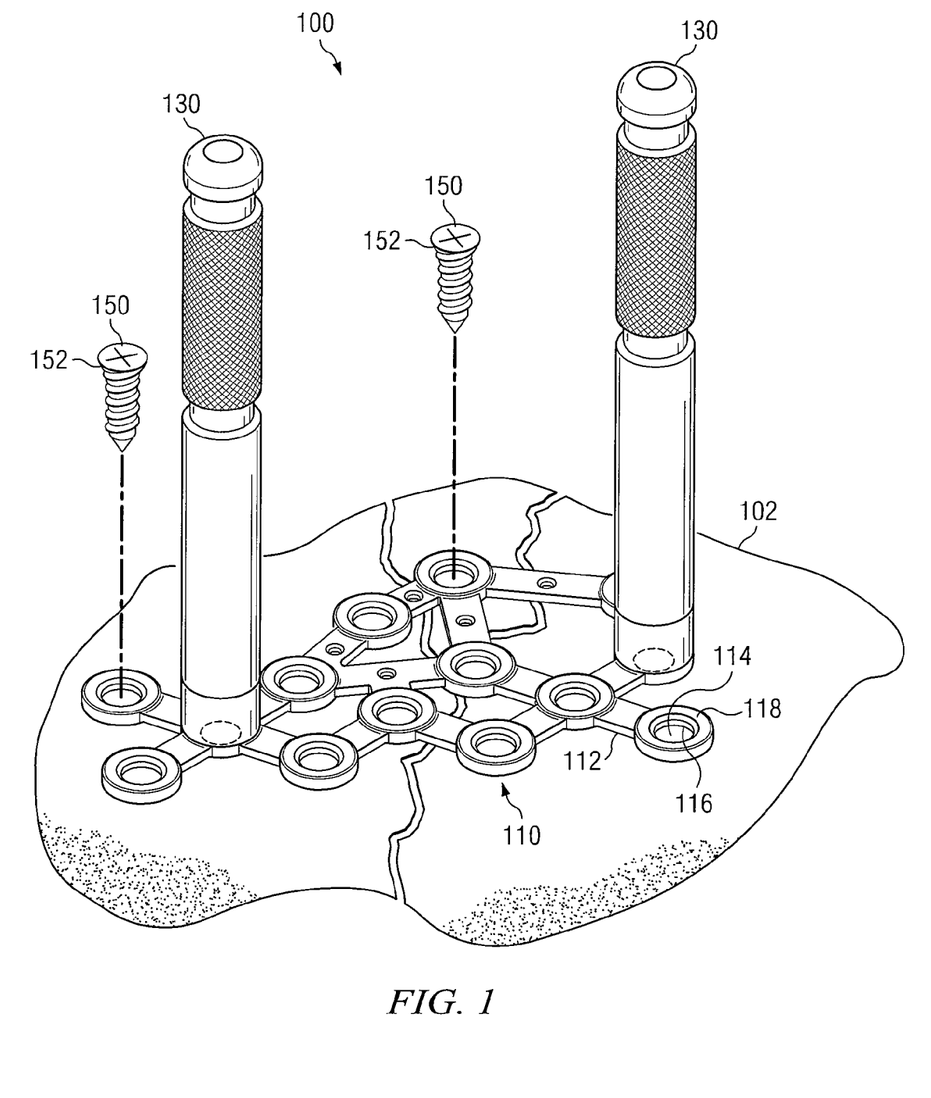
FIG. 1 illustrates an example embodiment of the present disclosure for contouring a locking plate to match the contours of a fractured bone.

FIG. 1 illustrates a system 100 for contouring a locking plate 110 to match the anatomy of a fractured bone 102 according to an example embodiment of the present disclosure. In the pictured embodiment, system 100 is being used relative to a single fractured bone 102; however, particular embodiments of system 100 may be applied equally as well to virtually any bone or group of bones in the body. For example, system 100 may be used to contour locking plate 110 to match the contours of bone 102 and another bone, or, bone 102 and a synthetic element such as a surgical implant. As an example use and not by way of limitation, system 100 may be used to contour locking plate 110 relative to a calcaneus in order to repair a calcaneal fracture.

In particular embodiments, system 100 may include locking plate 110, one or more benders 130, and one or more locking screws 150. Benders 130 may interlock with locking plate 110 such that a surgeon may use benders 130 to apply mechanical force to locking plate 110 in order to contour locking plate 110 to match the anatomy of bone 102 or to realign one or more segments of bone 102 along a desired contour. Benders 130 may be used to contour locking plate 110 even while locking plate 110 is coupled to bone 102, for example, by one or more locking screws 150. A surgeon may fasten benders 130 to virtually any part of locking plate 110 by screwing benders 130 into any one of a plurality of threaded screw holes 114 disposed throughout locking plate 110 and connected to one another by a plurality of ribs 112. Once benders 130 are fastened to locking plate 110, the surgeon may contour locking plate 110 by exerting mechanical force on benders 130 to bend locking plate 110 (e.g., to bend the ribs 112 of locking plate 110). Thinning ribs 112 may increase the chances that ribs 112 will bend during contouring and may reduce the chances that screw holes 114 will bend or deform during contouring.

In particular embodiments, a surgeon may couple locking plate 110 to bone 102 by inserting a locking screw 150 through one of threaded screw holes 114 and into bone 102, after which, the surgeon may contour locking plate 110 by using a single bender 130 to exert mechanical force on locking plate 110 relative to locking screw 150. Thus, bending of locking plate 110 may be achieved by manipulating one or more benders 130 as desired once benders 130 are fastened to locking plate 110. Since numerous threaded screw holes 114 may be spread out across the entirety of locking plate 110, a surgeon may shape virtually any portion of locking plate 110 using benders 130 even while locking plate 110 is coupled to bone 102. Once locking plate 110 has been satisfactorily contoured, locking plate 110 may be fully affixed to bone 102 by inserting a plurality of locking screws 150 into bone 102 through all or a subset of threaded screw holes 114.

In particular embodiments, system 100 may further include lockable pliers 170 having specially designed jaws 172 operable to capture and exert mechanical force on any one of threaded screw holes 114 without deforming the threads 116 of threaded screw holes 114. As an example and not by way of limitation, one of jaws 172 may contain a peg 174 that may be used to locate and align a screw hole 114 within jaws 172. When jaws 172 are closed, peg 174 may fit through screw hole 114 and into a corresponding cavity 176 in the opposing jaw 172. Pliers 170 may be used to contour locking plate 110 by clamping onto a rim 118 of a screw hole 114. Once jaws 172 are clamped down on rim 118, locking plate 110 may be bent (e.g., grossly bent) using pliers 170 without deforming threads 116.

In particular embodiments, pliers 170 may include a catch mechanism 182 that temporarily locks jaws 172 together when pliers 170 are closed. Thus, once jaws 172 are clamped onto a screw hole 114, a surgeon may use pliers 170 to bend locking plate 110 without having to constantly squeeze the handles of pliers 170 together in order to maintain a grip on screw hole 114.

In particular embodiments, locking plate 110 may be contoured using benders 130, pliers 170, or a combination thereof. As an example and not by way of limitation, system 100 may provide for easy contouring of locking plate 110 using either pliers 170 for gross bends outside the implant area (e.g., while the surgeon is holding locking plate 110) and/or benders 130 for bends within the implant area (e.g., while locking plate 110 is located in the incision area on bone 102) without deforming threads 116.

One of ordinary skill in the art will appreciate that the above-described embodiments of system 100 were presented for the sake of explanatory simplicity and will further appreciate that the present disclosure contemplates using any suitable combination and number of benders 130, locking screws 150, and pliers 170 to contour locking plate 110.

Figure 2:
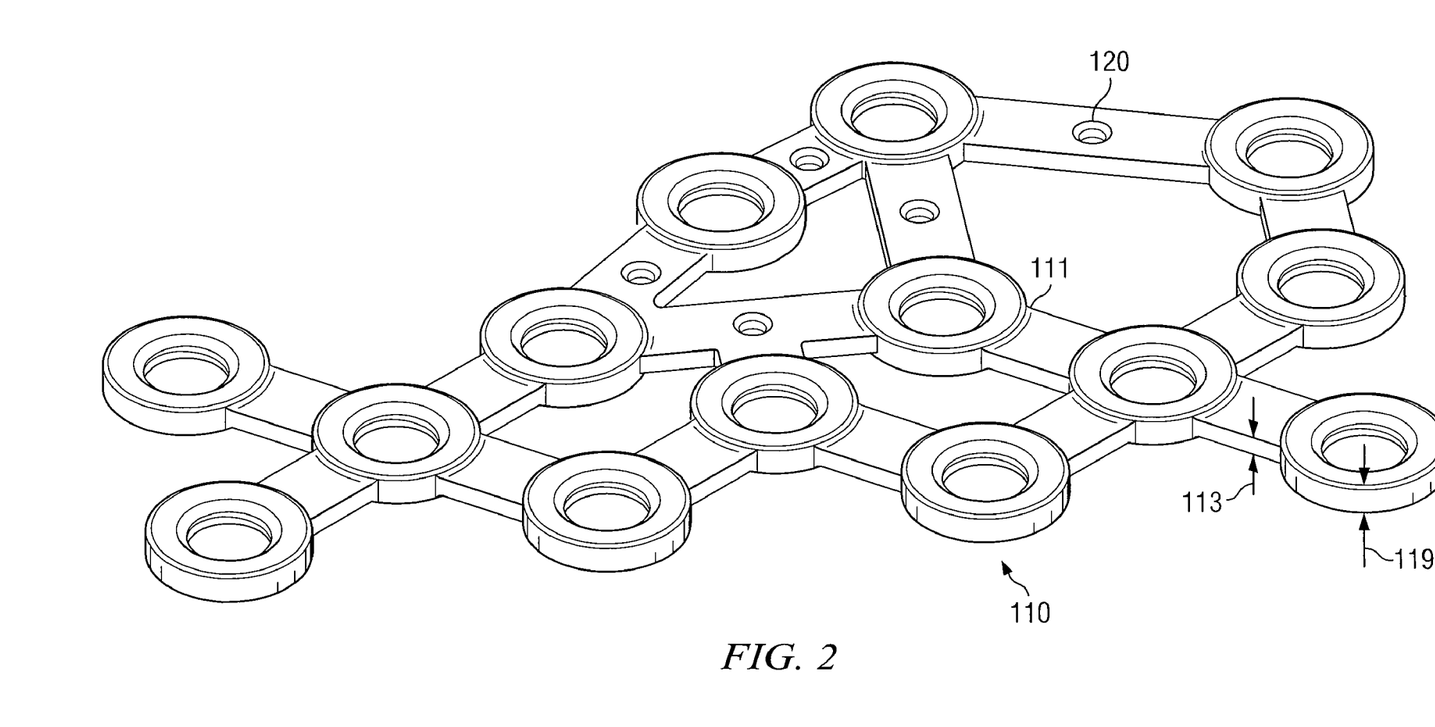
FIG. 2 illustrates an isometric view of an example embodiment of a locking plate.

FIG. 2 illustrates an isometric view of an example embodiment of locking plate 110. For reference purposes, locking plate 110 (as well as other components of system 100) may be referred to as having a top side intended to face away from bone segment 102 and a bottom side intended to face toward bone 102 (e.g., to be placed upon bone 102). Though particular features of locking plate 110 may be explained using such intended placement as a point of reference, this method of explanation is not meant to limit the scope of the present disclosure to any particular configuration of locking plate 110 or to any particular placement or orientation of locking plate 110 relative to bone 102 or any other components of system 100.

Locking plate 110 may include a body 111 comprising a plurality of threaded screw holes 114 connected to each other in a web-like distribution by a plurality of ribs 112. In particular embodiments, ribs 112 may be thinned down relative to threaded screw holes 114 to facilitate bending of ribs 112 rather than threaded screw holes 114 when locking plate 110 is contoured. As an example and not by way of limitation, a rib thickness 113 of each rib 112 may be less than a rim thickness 119 of the rim 118 of each threaded screw hole 114. Thinning ribs 112 such that rib thickness 113 is less that rim thickness 119 may increase the propensity of ribs 112 to bend during contouring rather than threaded screw holes 114, thereby preserving the geometry and integrity of screw holes 114. Thus, thinning ribs 112 may prevent screw holes 114 from warping when locking plate 110 is contoured. In particular embodiments, ribs 112 may only be thinned on the top side of locking plate 110, leaving the bottom side of locking plate 110 generally smooth. In particular embodiments, ribs 112 may be thinned on both the top and bottom sides of locking plate 110. In particular embodiments, ribs 112 may only be thinned on the bottom side of locking plate 110, leaving the top side of locking plate 110 generally smooth.

In particular embodiments, ribs 112 may comprise one or more positioning holes 120 that may be used to position locking plate 110 relative to bone 102. As an example and not by way of limitation, a surgeon may insert a K-wire into bone 102 after which the surgeon may position locking plate 110 on bone 102 by inserting the K-wire through positioning hole 120 and sliding locking plate 110 down onto bone 102. Additionally, the surgeon may rotate locking plate 110 about the K-wire using positioning hole 120 to achieve a desired orientation of locking plate 110 relative to bone 102. Once locking plate 110 has been properly positioned, the surgeon may secure locking plate 110 to bone 102, for example, by inserting one or more locking screws 150 into bone 102 through one or more threaded screw holes 114.

Each threaded screw hole 114 may be any threaded opening in locking plate 110 configured to threadably engage a locking screw 150 such that once locking screw 150 has been screwed into screw hole 114, locking screw 150 is prevented from rotating within screw hole 114. As an example and not by way of limitation, an inner surface of each of screw holes 114 may include locking threads 116 that interfere with a corresponding set of locking threads 152 on the head of locking screw 150. Once locking screw 150 is screwed into screw hole 114, locking threads 116 and/or locking threads 152 may deform to lock locking screw 150 into locking plate 110. In particular embodiments, locking threads 116 may be a set of double-helix threads on an inner surface of screw hole 114 while locking threads 152 may be a set of threads that extends onto the head of locking screw 150. By lockably engaging locking screws 150 using, for example, thread interference, screw holes 114 may hinder or prevent locking screws 150 from backing out of locking plate 110.

In particular embodiments, each threaded screw hole 114 may comprise a rim 118. Rim 118 may comprise a flat surface surrounding each threaded screw hole 114. When bender 130 is screwed into a threaded screw hole 114, rim 118 may abut a shoulder 132 of bender 130. Thus, once bender 130 has been screwed into screw hole 114, shoulder 132 may rest flush against rim 118 enabling bender 130 to exert mechanical force on locking plate 110 through rim 118. One of ordinary skill in the art will appreciate that the above-described embodiments of locking plate 110 were presented for the sake of explanatory simplicity and will further appreciate that the present disclosure contemplates any suitable configuration and number of screw holes 114, threads 116, ribs 112, and positioning holes 120 in locking plate 110.

Figure 3:
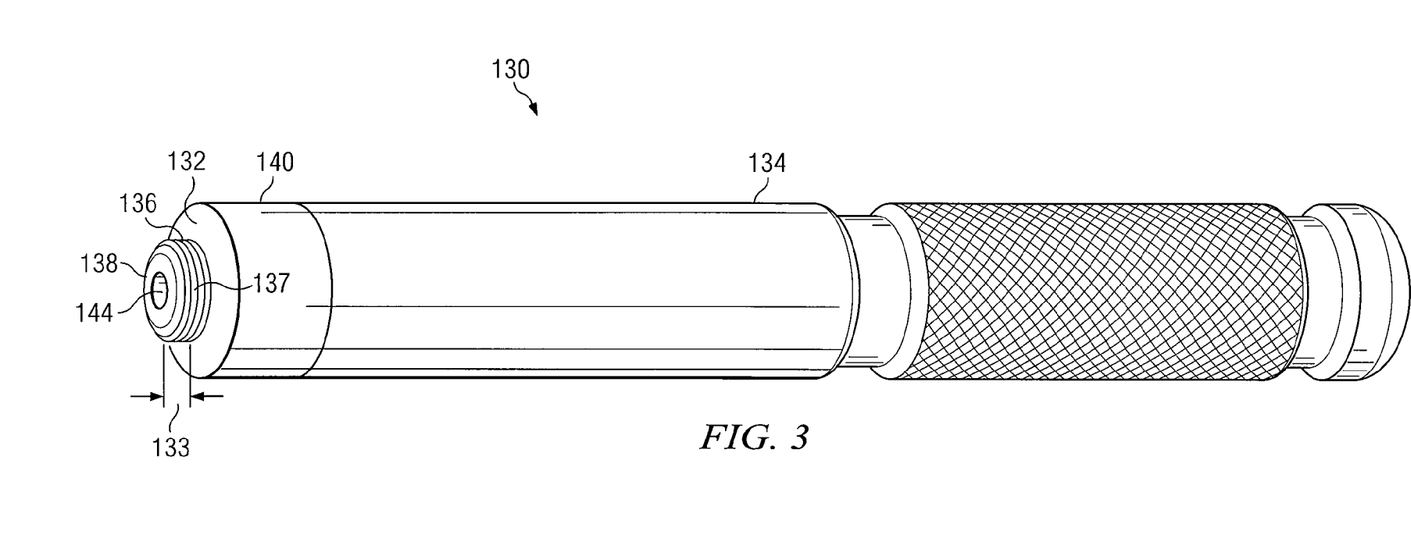
FIG. 3 illustrates an isometric view of example embodiment of a bender that may be used to contour the locking plate of FIG. 2.

FIG. 3 illustrates an isometric view of an example embodiment of bender 130. Bender 130 may include a shaft 134, a shoulder 132, and a threaded tip 136. In particular embodiments, bender 130 may be fastened to locking plate 110 by screwing threaded tip 136 into a threaded screw hole 114 of locking plate 110 until shoulder 132 rests against the top surface of locking plate 110 (e.g., the top surface of a rim 118). One unique feature of bender 130 is shoulder 132, which may directly rest against locking plate 110; thus, shoulder 132 may serve as a feature used to apply mechanical force to locking plate 110 in order to create one or more desired bends in locking plate 110.

In particular embodiments, shoulder 132 may comprise a smooth flat surface surrounding threaded tip 136. When threaded tip 136 is screwed into threaded screw hole 114, shoulder 132 may abut rim 118 and act as a stop which limits the maximum penetration of threaded tip 136 into a screw hole 114. Once shoulder 132 is in contact with the top surface of rim 118, shoulder 132 may transmit a majority of the mechanical force from bender 130 to locking plate 110 during contouring. Threads 137 may transmit only a minority (e.g., a negligible amount) of the mechanical force to locking plate 110 when shoulder 132 is in contact with the top surface of rim 118. By using shoulder 132 to transmit a majority of the mechanical force from bender 130 to locking plate 110 during contouring, system 110 may allow a surgeon to exert substantial mechanical force on locking plate 110 using bender 130 without stripping out or deforming screw holes 114. Furthermore, since shoulder 132 may rest flush against the top surface of rim 118, shoulder 132 may transmit mechanical force across rim 118 in an approximately equal distribution thereby preventing screw hole 114 (e.g., rim 118) from warping due to unequal force distribution.

If bender 130 did not include shoulder 132, but instead employed threads 137 as the primary mechanism to transmit mechanical force to locking plate 110, there would be a greater chance that a surgeon could strip out the threading of screw holes 114 (e.g., threads 116) or otherwise warp screw holes 114 while contouring locking plate 110. For example, bending locking plate 110 with a shoulder-less bender could deform threads 116 in locking plate 110 to such a point that threads 116 could not engage the locking threads 152 of locking screw 150. Consequently, using a bender without a shoulder to apply force directly to the threaded region of locking plate 110 (e.g., threads 116), may lead to thread deformation in locking plate 110 as well as warping of screw holes 114, and ultimately to less than desirable locking screw engagement into locking plate 110.

In particular embodiments, bender 130 may enable a surgeon to press locking plate 110 directly against bone 102 to achieve precise contouring. For example, a length 133 of threaded tip 132 (e.g., the distance between end 138 of threaded tip 136 and shoulder 132) may be less than or equal to rim thickness 119. Consequently, when threaded tip 136 is screwed into screw hole 114, shoulder 132 may prevent any significant portion of threaded tip 136 from extending through the bottom side of screw hole 114. In particular embodiments, end 138 may comprise a flat surface that rests approximately flush with the bottom side of locking plate 110 when threaded tip 136 is fully engaged with screw hole 114. Since end 138 rests approximately flush with the bottom surface of locking plate 110 when threaded tip 136 is fully engaged with screw hole 114, bender 130 is operable to press the bottom surface of locking plate 110 directly against a top surface of bone 102.

If bender 130 did not include shoulder 132 to act as a stop for threaded tip 136, or if any significant portion of tip 136 (e.g., greater than 1 or 2 millimeters) otherwise extended through screw hole 114 when bender 130 was fully engaged with screw hole 114, a surgeon could likely not use bender 130 to press the bottom surface of locking plate 110 directly against bone 102 due to the portion of tip 132 extending through threaded screw hole 114. Rather the surgeon would likely have to remove bender 130 from locking plate 110 in order to press locking plate 110 against the surface of bone 102.

In particular embodiments, bender 130 may be cannulated to allow K-wires or drill bits to be placed onto bone 102 through bender 130. As an example and not by way of limitation, a K-wire or drill bit may be placed through a cannula 144 in bender 130 once final bending of a particular screw hole 114 hole has been completed to anchor locking plate 110 to bone 102 at the completed screw hole location. As an additional example and not by way of limitation, a surgeon may position a K-wire in bone 102 and then place locking plate 110 over the K-wire using one of screw holes 114. After the surgeon has positioned locking plate 110 relative to bone 102 using screw hole 114 as a pivot point, the surgeon may slide bender 130 over the K-wire using the K-wire as a guide to align bender 130 with screw hole 114 one bone 102.

Figure 4:
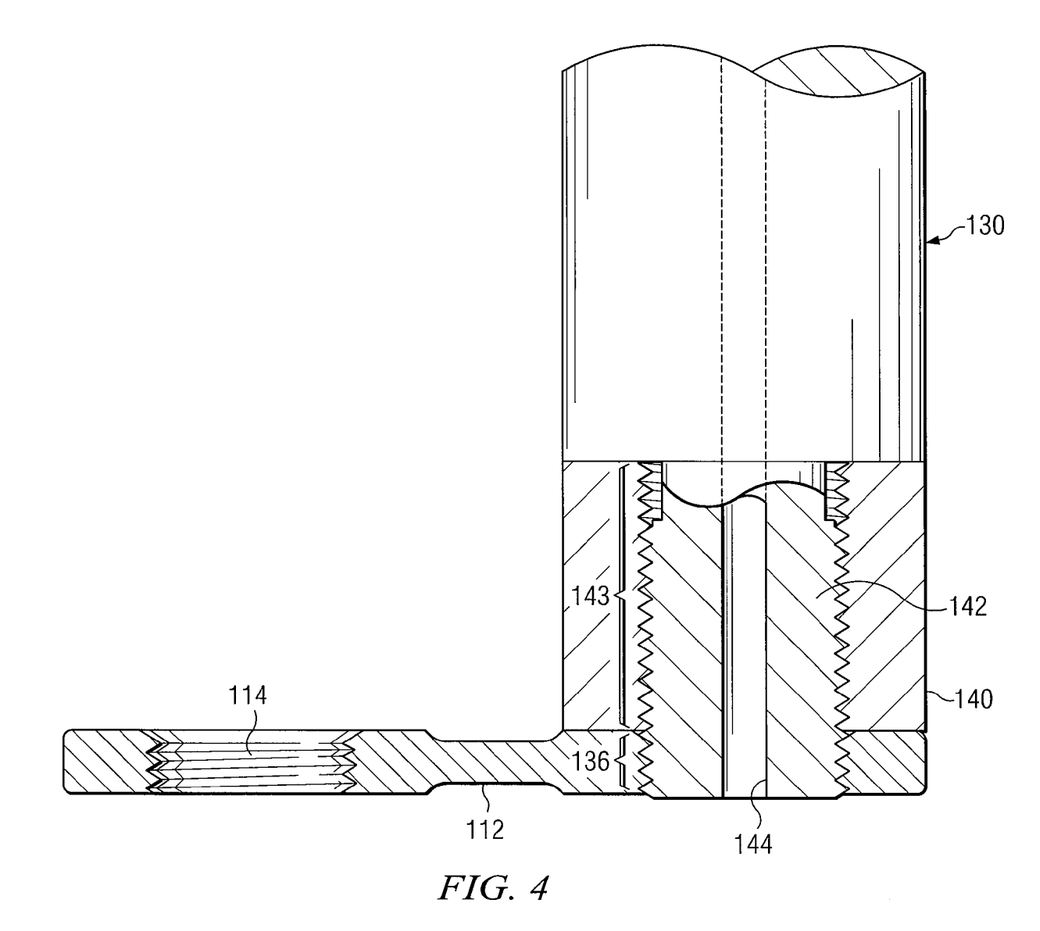
FIG. 4 illustrates an example cross section view of the bender of FIG. 2 engaged with the locking plate of FIG. 3.

FIG. 4 illustrates an example cross section view of bender 130 engaged with locking plate 110. Once bender 130 is fully engaged with locking plate 110 (e.g., once threaded tip 136 is fully screwed into screw hole 114), end 138 may rest approximately flush with the bottom surface of locking plate 110 (e.g., the bottom surface of rim 118) and shoulder 132 may rest substantially flush against rim 118. In particular embodiments, a small portion of threaded tip 136 (e.g., approximately 0.5 millimeters) may extend beyond the bottom surface of locking plate 110; however, such portion may be considered negligible when pressing locking plate 110 against bone 102 using bender 130 insofar as it does not hinder a surgeon from placing a portion of locking plate 110 disposed beneath bender 130 in contact with bone 102.

In particular embodiments, threaded tip 136 may be formed by the union of a shoulder piece 140 with a threaded extension 142 of shaft 134. As an example and not by way of limitation, bender 130 may include a shaft 134 having a threaded extension 142 and a shoulder piece 140 engaged with a first portion 143 of threaded extension 142 such that a second portion of threaded extension 142 extends through shoulder piece 140 to form the threaded tip 136 of bender 130. More particularly, shoulder piece 140 may comprise a cylindrical nut having a threaded inner surface that screws over threaded extension 142. After shoulder piece 142 has been screwed onto extension 142 such that threaded tip 136 is exposed, shoulder piece 140 may be secured to extension 142 using, for example, medical grade epoxy.

Forming threaded tip 136 out of shoulder piece 140 and extension 142 allows the threads 137 of threaded tip 136 to extend all the way from end 138 to the very edge of shoulder 132. More particularly, this manner of forming threaded tip 136 may eliminate the need to provide tooling tolerances on threaded tip 136 to accommodate the threading tools used to create threads 137. Since the threaded portion of screw hole 114 may be relatively shallow (e.g., less than ⅛ of an inch), it may be advantageous for threads 137 to cover the entirety of threaded tip 136 to ensure that threaded tip 136 has enough purchase in screw hole 114 to hold fast during contouring.

One of ordinary skill in the art will appreciate that the above-described method of forming threaded tip 136 was presented for the sake of explanatory simplicity and will further appreciate that the present disclosure contemplates any suitable method of forming a threaded tip 136 on bender 130 such that threaded tip 136 is operable to threadably engage locking plate 110 (e.g., via screw hole 114).

Figure 5:
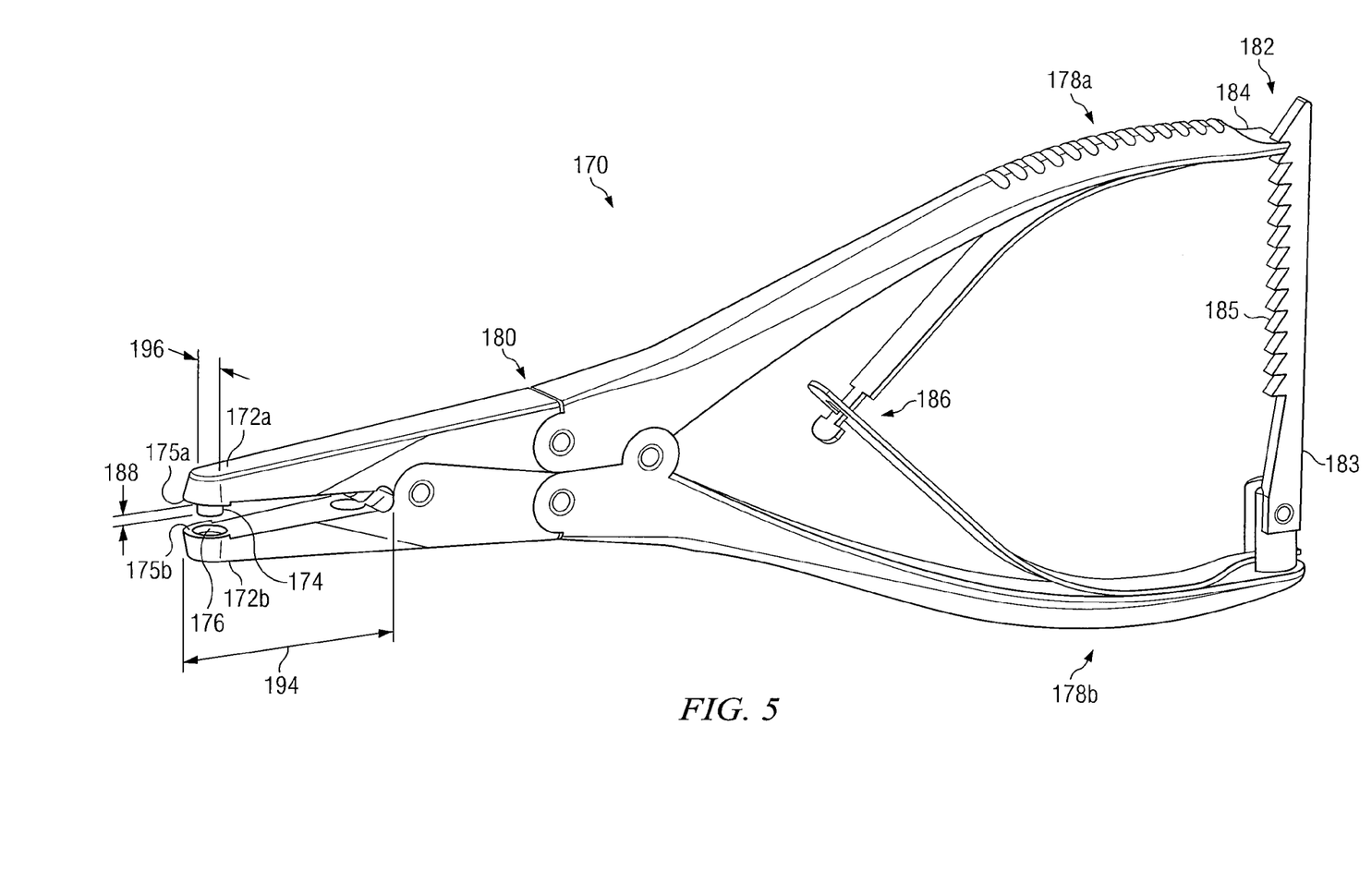
FIG. 5 illustrates an isometric view of an example embodiment of a pliers that may be used to contour the locking plate of FIG. 2.

FIG. 5 illustrates an isometric view of an example embodiment of a pliers 170 that may be used to contour locking plate 110. Pliers 170 includes a first handle 178a and a second handle 178b coupled to jaws 172a and 172b through a hinge mechanism 180. Pliers 170 further includes a catch mechanism 182 disposed between handles 178a and 178b operable in conjunction with a spring mechanism 186 to temporarily lock jaws 172 together when pliers 170 are closed.

Catch mechanism 182 may be any mechanical fixture or device or combination of two or more such devices capable of lockably positioning jaw 172a relative to jaw 172b. As an example and not by way of limitation, catch mechanism 182 may comprise a ratchet arm 183 having a plurality of notches 185 that interlock with a flattened tip 184 of one of handles 178 such that catch mechanism 182 temporarily prevents handles 178 from drawing apart unless catch mechanism 182 is unlocked (e.g., unless ratchet arm 183 is lifted from flattened tip 184). By lockably positioning handle 178a relative to handle 178b, catch mechanism 182 may be used to lockably position jaw 172a relative to jaw 172b through hinge 180. In particular embodiments catch mechanism 182 may be aided by a spring mechanism 186 which exerts a constant separating tension on handles 178 to hold handles 178 apart (e.g., to press flattened tip 184 into one of notches 185 of ratchet arm 183).

Spring mechanism 186 may be any mechanical device or fixture or combination of such devices or fixtures operable to exert outward mechanical tension on handles 178 such that handle 178a is pushed away from handle 178b by the tension exerted by spring mechanism 186. In particular embodiments, when a surgeon squeezes handles 178 together with enough strength to over come the tension exerted by spring mechanism 186, handle 178a will move toward handle 178b causing jaw 172a to move toward jaw 172b. As handles 178 move toward one another, flattened tip 184 may progressively transition along the notches 185 of ratchet arm 183. When the surgeon ceases squeezing handles 178 together, spring mechanism 186 may exert separating tension on handles 178 holding flattened tip 184 in tension against one of notches 185.

In particular embodiments, the jaws 172 of pliers 170 may include a pair of lips 175 operable to capture one of screw holes 114. As an example and not by way of limitation, when jaws 172 are placed over locking plate 110 such that peg 174 aligns with a screw hole 114, jaws 172 may capture the screw hole 114 by sandwiching rim 118 between lips 175. Once lips 175 are in contact with the top and bottom surface of rim 118, lips 175 may transmit a majority of the mechanical force from pliers 170 to locking plate 110 during contouring while peg 174 may transmit only a minority (e.g., a negligible amount) on none of such force to locking plate 110. Thus, pliers 170 may be used to contour locking plate 110 without deforming threads 116 of threaded screw holes 114.

In particular embodiments, peg 174 may limit a minimum separation distance between lips 175 when jaws 172 are closed. As an example and not by way of limitation, a length 188 of peg 174 may be configured such that when jaws 132 are fully closed (e.g., when peg 174 abuts the opposing jaw 172), a minimum separation distance between lips 175 is approximately equal to rim thickness 119. Thus, when jaws 132 are clamped on to a particular screw hole 114, peg 174 may abut the opposing jaw 172 at approximately the same time as lips 175 come in contact with rim 118. In particular embodiments, catch mechanism 182 may be configured to lock jaws 172 in the closed position (e.g., in a position such that lips 175 are clamped onto rim 118). For example, catch mechanism 182 may work in conjunction with peg 174 to maintain a proper clearance between jaws 170 (e.g., lips 175) to sandwich locking plate 110 when pliers 170 are fully closed.

In particular embodiments a length 194 of jaws 194 may be relatively long (e.g., an inch or more) to allow jaws 172 to reach screw holes 114 located near the center of locking plate 110. In particular embodiments a width 196 of jaws 172 may taper from narrow to wide as one progresses along the length 194 of jaws 172 from peg 174 toward hinge mechanism 180. As an example and not by way of limitation, the width 196 of the tips of jaws 172 may be equal to a diameter of rim 118 to enable pliers 170 to work in close proximity to a bender 130 or another pliers 170 while engaged with locking plate 110.

Although the present disclosure has been described in several embodiments, a myriad of changes, substitutions, and modifications may be suggested to one skilled in the art, and it is intended that the present disclosure encompass such changes, substitutions, and modifications as fall within the scope of the present appended claims.

What is claimed is:

1. A system for contouring a locking plate, comprising:
   a locking plate that includes a plurality of threaded screw holes connected to one another by one or more ribs;
   at least one bender that includes:
      a threaded tip configured to threadably engage one or more of the plurality of threaded screw holes; and
      a shoulder operable to transmit mechanical force to the locking plate once the threaded tip is threadably engaged with one of the plurality of threaded screw holes;
      wherein the at least one bender comprises a shaft having a threaded extension and a shoulder piece threadably engaged with a first portion of the threaded extension such that a second portion of the threaded extension extends through the shoulder piece to form the threaded tip of the bender; and
   wherein a thickness of each of the one or more ribs is less than a thickness of a rim surrounding each of the plurality of threaded screw holes to facilitate bending of the ribs when the mechanical force is applied to the locking plate.

2. The system of claim 1, wherein once the threaded tip is threadably engaged with one of the plurality of threaded screw holes, the shoulder is operable to transmit a majority of the mechanical force from the bender to the locking plate and the threaded tip is operable to transmit a minority of the mechanical force to the locking plate.

3. The system of claim 1, wherein:
the shoulder comprises a first flat surface surrounding the threaded tip; and
the shoulder is operable to transmit mechanical force to the locking plate once the threaded tip is threadably engaged with one of the plurality of threaded screw holes by abutting an opposing flat surface of a rim surrounding the threaded screw hole.

4. The system of claim 1, wherein a length of the threaded tip is less than or equal to a thickness of a rim surrounding each of the plurality of threaded screw holes.

5. The system of claim 1, wherein:
the shoulder generally prevents the threaded tip from extending through one of the plurality of threaded screw holes once the threaded tip is threadably engaged with the screw hole; and
a bottom portion of the threaded tip is flattened such that the bottom portion rests approximately flush with a bottom surface of the locking plate once the threaded tip is threadably engaged with the screw hole.

6. The system of claim 5, wherein the at least one bender is operable to press a bottom surface of the locking plate directly against a top surface of a bone once the threaded tip is threadably engaged with one of the plurality of threaded screw holes.

* * * * *